(12) United States Patent
Gitelis

(10) Patent No.: US 7,020,925 B1
(45) Date of Patent: Apr. 4, 2006

(54) MECHANICAL TOOTHBRUSH

(75) Inventor: Meir Gitelis, Moshav Bnei Atarot (IL)

(73) Assignee: Avtipus Patents & Inventions Ltd., Moshav Bnei Atarot (IL)

( * ) Notice: Subject to any disclaimer, the term of this patent is extended or adjusted under 35 U.S.C. 154(b) by 0 days.

(21) Appl. No.: 10/905,262

(22) Filed: Dec. 22, 2004

(51) Int. Cl.
*A61C 17/40* (2006.01)
*A60C 17/22* (2006.01)

(52) U.S. Cl. .......................................... 15/22.1; 15/28

(58) Field of Classification Search ............... 15/22.1, 15/22.2, 22.4, 28
See application file for complete search history.

(56) References Cited

U.S. PATENT DOCUMENTS 4,027,348 A * 6/1977 Flowers et al. ............... 15/22.1
4,791,945 A * 12/1988 Moriyama ................... 15/22.1

FOREIGN PATENT DOCUMENTS

DE 3529861 * 2/1987
WO 2004041114 * 5/2004

* cited by examiner

*Primary Examiner*—Gary K. Graham
(74) *Attorney, Agent, or Firm*—Haim Factor

(57) ABSTRACT

A toothbrush distal end for attachment to a handle of a mechanical toothbrush; the distal end comprising: a head; a neck having a proximal end and a distal end; a drive shaft having a driving bevelled gear fixed to distal end thereof; a brush consisting of a bristle array on a brush back plate, and a movement; the head being fixedly attached to the distal end of the neck; the neck being fixedly couplable to the handle and the drive shaft being couplable to a driving means; the neck being hollow and serving as a sleeve for the drive shaft; the drive shaft being rotatingly drivable about its axis within the neck, by the driving means; wherein the movement is situated within a cavity in the head and is connected to the brush back plate, for moving the brush back plate along an eccentric orbital path with respect to the head when driven by the driving means via the rotating drive shaft.

14 Claims, 4 Drawing Sheets

MECHANICAL TOOTHBRUSH

FIELD OF THE INVENTION

The present invention is directed to providing a brush and a head unit for a mechanical toothbrush, typically an electrical toothbrush that enables a brushing effect similar to that obtained using manual toothbrushes.

BACKGROUND OF THE INVENTION

To prevent tooth decay, the advantages of regular brushing have long been recognized. The optimal brushing technique is to move the toothbrush bristles in small orbital movements. This may be accomplished using manual toothbrushes having the toothbrush head and bristles thereon fixed to the neck of the brush, by the brusher moving his hand in small circles.

To provide a large number of brush strokes in small time periods, electric toothbrushes are often used. These are configured somewhat differently however, usually having a circular bristle array that rotates about its axis. Such a brushing motion is inherently inferior to the small orbital brush strokes of the manual operated toothbrush, and the brush head is typically rather smaller than that of manual toothbrushes, resulting in only one or two teeth being brushed at one time. However the larger number of brush strokes obtainable by electrical toothbrushes goes a long way to overcome this disadvantage.

Recent developments in manual toothbrushes combine different bristle types. For example, one combination has outer layers of soft bristles or rubber spikes to massage gums and inner layers of hard nylon bristles for scraping enamel surfaces of teeth, to remove plaque and scale. It will be appreciated, that such combinations are not obtainable on rotating circular brush heads, and thus are not provided by electrical toothbrushes.

There have been several attempts to obtain the effect of manual brushing with electrical toothbrushes, and there are several hundred electrical toothbrushes in the prior art. Some have two drive systems to move the brush head back and forth in two direction pairs, substantially perpendicular to each other and to the bristles themselves. Such motorized toothbrushes either brush in both direction pairs simultaneously but at different frequencies, or can be operated to brush in one direction pair, such as from side to side with respect to the toothbrush handle, and then in the other direction pair, such as inwards and outwards with respect to the toothbrush handle. Some prior art toothbrushes use piezoelectric chips to drive the toothbrush head back and forth ultrasonically. Most use simple rack and pinion gears.

Combination toothbrushes with fixed bristle arrays and rotating bristle array are also known. These go some way to providing the advantages of both electrical and manual brushing in a single toothbrush. However, in general, electrical toothbrushes have not superseded manual toothbrushes because none provide the effects of the preferred circular strokes of correct manual brushing in a reliable manner.

U.S. Pat. No. 4,791,945 to Moriyama describes a power operated toothbrush including a brush supporting arm which is pivoted on two crank means. The distance between a crank shaft and a crank pin of one of the crank means is continuously changed so that the turning motion or oscillatory motion of a brush member which is mounted on an end of the brush supporting arm can be produced and one of the motions can be continuously changed to the other. One embodiment described therein is a power operated toothbrush including a hollow casing, an electric motor within the casing, means for energizing the electric motor, a pair of cranks spaced apart longitudinally of the hollow casing having eccentric drive pins thereon, means for rotating the cranks the same amount and at the same speed from the electric motor including bevelled gears secured to the motor and to one of the cranks, a spur gear on each of the cranks and a series of spur gears connecting the cranks to each other for simultaneous similar rotation, a toothbrush member having bristles on one end thereof, means for securing the other end of the toothbrush member to one of the cranks and means for securing the other of the cranks to the toothbrush member centrally thereof and means operably associated with at least one of the cranks for varying the eccenticity of the eccentric pin thereon to vary the motion of the bristles of the toothbrush between a complete circular orbital motion and a reciprocal arcuate motion. The toothbrush described therein can be set to achieve the desired orbital brushing, since the neck of the toothbrush can be set to reciprocate in an elliptical manner with regards to the handle. However, since the large neck and head move backwards and forwards, a large motor is required and the power drain on the batteries is considerable. Such toothbrushes are impractical, expensive to manufacture and liable to failure, not least because of the difficulty of sealing the handle against moisture penetration.

Ideally, therefore, a mechanical toothbrush having a head with a rectangular array of bristles thereon, is required, such that the rectangular array of bristles is driven by a mechanism in an orbital path simulating the movement imparted to the toothbrush head and bristle array of a manual toothbrushes operated in a correct brushing manner by the user, and the present invention provides such a mechanical toothbrush.

SUMMARY OF THE INVENTION

It is an aim of the preferred embodiments, that a mechanical toothbrush is provided, that has an automated brushing movement similar to that obtained by correct manual brushing.

It is a further aim of the preferred embodiments, that the bristles be configured such that a relatively large area of the teeth may be brushed at once, similar to the state of affairs with manual toothbrushes.

It is a further aim of embodiments wherein the mechanical toothbrush is battery driven, that only a small, lightweight section is moved only a small amount, thereby conserving energy and prolonging battery life.

The present invention is directed to providing a toothbrush distal end for attachment to a handle of a mechanical toothbrush; the distal end comprising: a head; a neck having a proximal end and a distal end; a drive shaft having a driving bevelled gear fixed to distal end thereof; a brush consisting of a bristle array on a brush back plate, and a movement; the head being fixedly attached to the distal end of the neck; the neck being fixedly couplable to the handle and the drive shaft being coupleable to a driving means; the neck being hollow and serving as a sleeve for the drive shaft; the drive shaft being rotatingly drivable about its axis within the neck, by the driving means; wherein the movement is situated within a cavity in the head and is connected to the brush back plate, for moving the brush back plate along an eccentric orbital path with respect to the head when driven by the driving means via the rotating drive shaft.

In preferred embodiments, the movement comprises a driven bevelled gear, a master gear, a transmission system and a slave gear, with eccentric pins being eccentrically attachable to the master and slave gears, for attachment of the brush back plate to said eccentric pins; the driven bevelled gear being drivenly coupled to the driving bevelled gear of the drive shaft; the driven bevelled gear being coupled to the master gear, such that driven bevelled gear drives master gear and master gear drives slave gear via transmission, for rotating master gear and slave gear together in same direction; the eccentric pins driving brush in an eccentric orbital path.

In preferred embodiments, the transmission is an intermediate gear, said master gear, intermediate gear and slave gear rotate around axles that engage inside back wall of the cavity in the toothbrush head; the driven bevelled gear is coaxially joined to the master gear; each eccentric pin passing through an aperture in face of toothbrush head, and connect to back of brush back plate.

Optionally the axles are fixedly connected to back of toothbrush head and said master, slave and intermediate gears freely rotate round their axles.

Alternatively, the axles are fixedly connected to master, slave and intermediate gears and loosely engage sockets on back of toothbrush head, freely rotating with respect to said sockets.

Optionally the eccentric pins are fixedly connected to said master and slave gears and loosely engage holes on brush back plate. Preferably the eccentric pins are split pins that clip fit into said holes.

Alternatively, the eccentric pins are fixedly connected to said brush back plate and loosely engage socket holes in said master, slave and intermediate gears, freely rotating with respect to said socket holes. Preferably the eccentric pins are split pins that clip fit said socket holes.

Typically the driving means comprise a motor and power source.

Optionally and preferably the motor and power source are situated within said handle. Typically the power source being selected from the list of: a power supply coupled to an electric main, a one use battery and a rechargeable battery.

However, alternatively the driving means is selected from the list of hydraulic driving means, pneumatic driving means and electrical driving means, the distal end connecting to a handle of a professional dental tool.

Optionally the toothbrush distal end is permanently fixed to a handle. Alternatively, the toothbrush distal end is removably attachable to a handle.

BRIEF DESCRIPTION OF THE DRAWINGS

For a better understanding of the invention and to show how it may be effected, reference is made, to the accompanying drawings, which show a preferred embodiment of the present invention. No attempt is made to show structural details of the invention in more detail than is necessary for a fundamental understanding of the invention; the description taken with the drawings making apparent to those skilled in the art how the several forms of the invention may be embodied in practice. The same numbers are used to annotate the same parts, throughout the drawing set.

In the accompanying drawings.

DETAILED DESCRIPTION OF THE EMBODIMENTS

Figure 1:
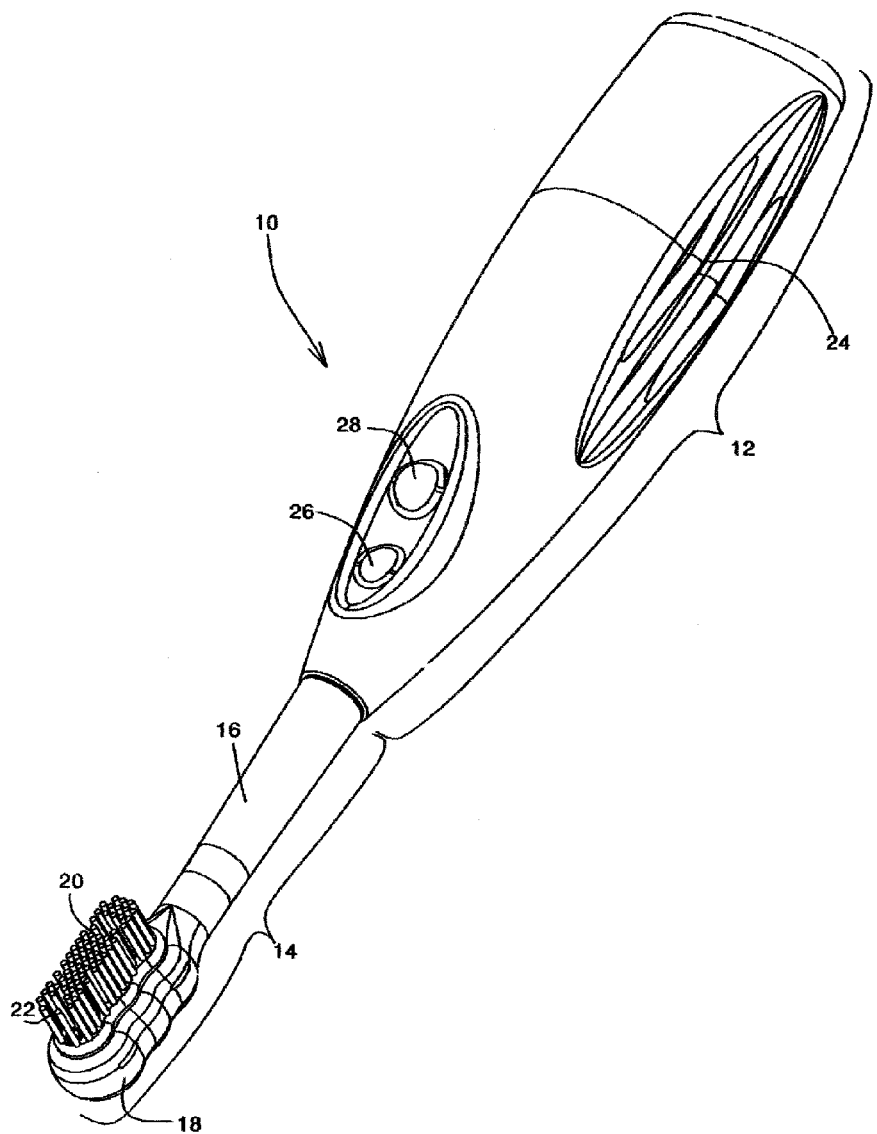
FIG. 1 is an isometric projection of a battery operated electrical toothbrush consisting of a handle and a distal toothbrush end in accordance with a preferred embodiment of the present invention.

Referring now to FIG. 1, an isometric projection of a battery operated electrical toothbrush 10 consisting of a proximal handle 12 and a distal toothbrush end 14. The distal toothbrush end 14 consists of a neck 16, a head 18 with a brush 20 attached thereto; the brush typically consisting of bundles of bristles. The handle 12 may have a non-slip gripping section 24 attached thereto, and will typically have ON 26 and OFF 28 push button switches conveniently situated for operation by the user.

Figure 2:
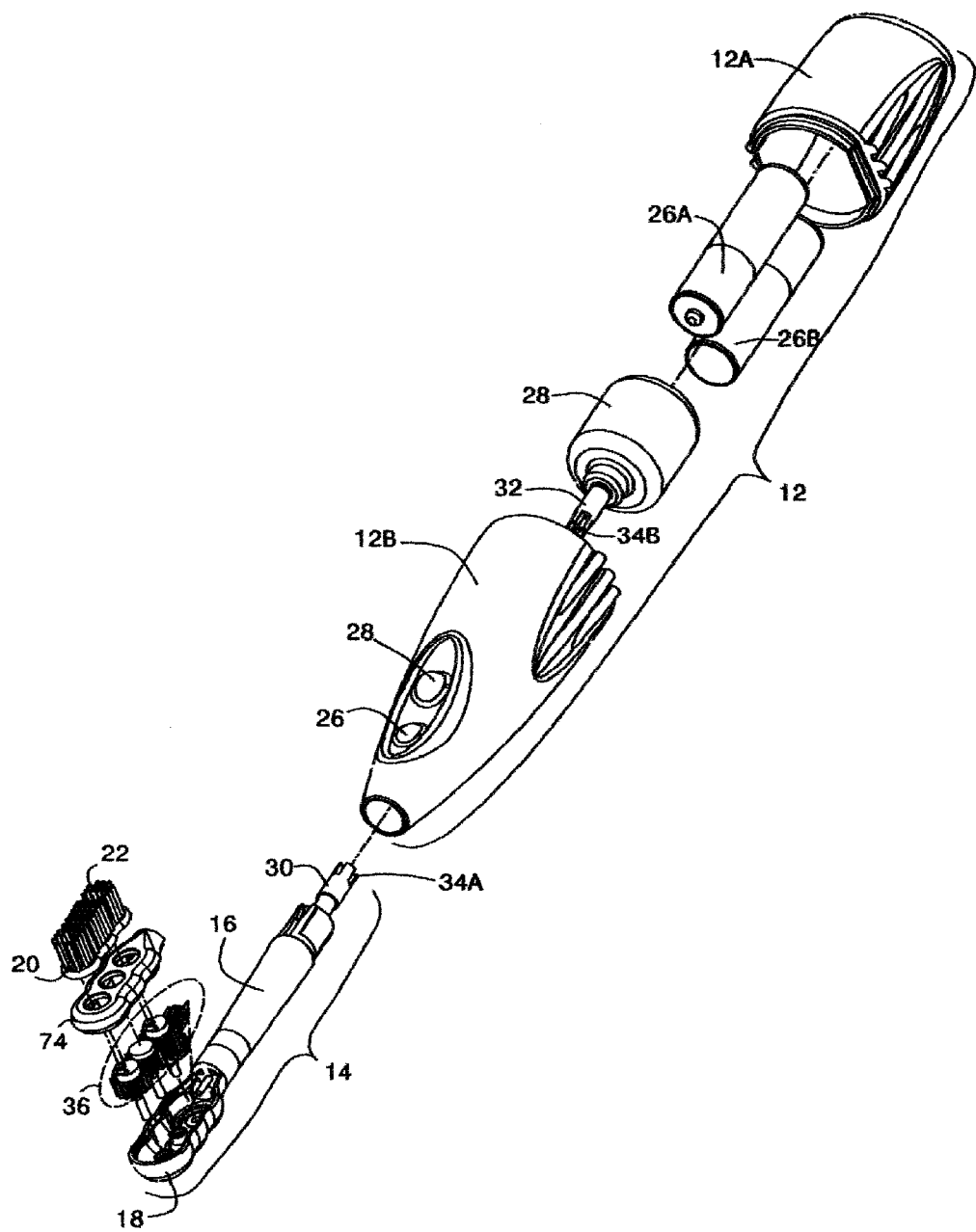
FIG. 2 is an exploded isometric view of the battery operated electrical toothbrush shown in FIG. 1.

As shown in FIG. 2, the handle 12 will typically consist of two pieces 12A, 12B that come apart. Within the handle 12, one or more voltaic cells (batteries) 26A. 26B are provided, which power a motor 28. A drive shaft 30, within the distal toothbrush end 14 engages the spindle 32 of the motor 30, typically via a coupling 34A, 34B.

When the battery operated electrical toothbrush 10 is switched ON, the batteries 26A, 26B provide power to the motor 28 that rotates the drive shaft 30. Optionally, a gearbox will be provided between motor 28 and drive shaft 30, such that the angular velocity of the drive shaft 30 may be set as desired. Batteries 26A, 26B may be single use, disposable batteries or rechargeable batteries, and such handles 12 are known. In contradistinction to the distal toothbrush ends of the prior art however, distal toothbrush end 14 includes a movement 36 that drives the brush 20 in a continuous orbital path similar to that obtained by correct manual brushing.

Figure 3:
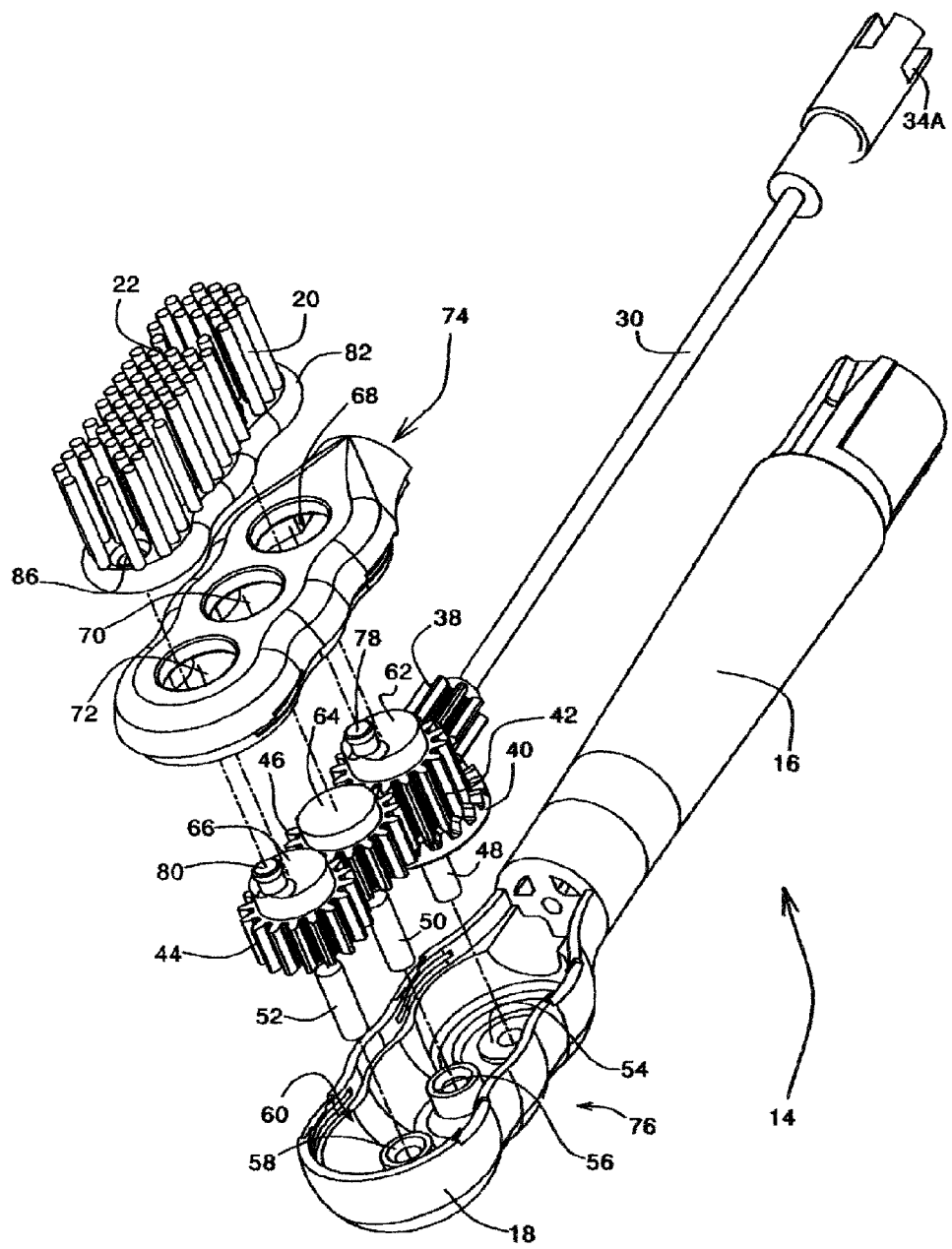
FIG. 3 is an exploded isometric view of the distal toothbrush end of one embodiment the present invention having eccentric pins permanently fixed to master and slave gears and engaging socket holes in brush back plate of brush.

With reference to FIG. 3, distal toothbrush end 14 of one embodiment of the present invention is shown in exploded detail. The neck 16 is hollow sleeve, through which the drive shaft 30 passes. A driving bevelled gear 38 couples to a driven bevelled gear 40 that is coaxial to a master gear 42. A slave gear 44 is coupled to the master gear 42 by a transmission system, typically an intermediate gear 46, which ensures that the master gear 42 and slave gear 44 rotate together in the same direction.

The master gear 42, slave gear 44 and intermediate gear 46 rotate about axle pins 48, 50, 52 that engage sockets 54, 56, 58 in the inner back 60 of the toothbrush head 18. The master, slave and intermediate gears 42, 44, 46 either freely rotating around their axles 48, 50, 52, or being fixed to axles, 48, 50, 52, which themselves are free to rotate in sockets 54, 56, 58. The faces 62, 64, 66 of the master, slave and intermediate gears 42, 44, 46 respectively, freely rotate in holes 68, 70, 72 in a facing plate 74 that fits to back 76 of head 18, typically by being press fitted there onto.

Eccentric pins 78, 80 protrude from the master and slave gears 42, 44 and connect to the brush back plate 82 of the brush 20, by engaging socket holes 84, 86 in brush back plate 82 of brush 20. The eccentric pins 78, 80 drive the brush 20 in an eccentric orbital path that provides the correct brushing technique, hitherto obtainable only via manual brushing.

Since the bevelled driving gear 38 tends to intermesh with the beveled driven gear 40 from above, essentially coplanar with the master gear 42, the overall thicken of the toothbrush head 18 may be kept thin, whilst nevertheless, allowing the gears themselves to be quite substantial.

Figure 4:
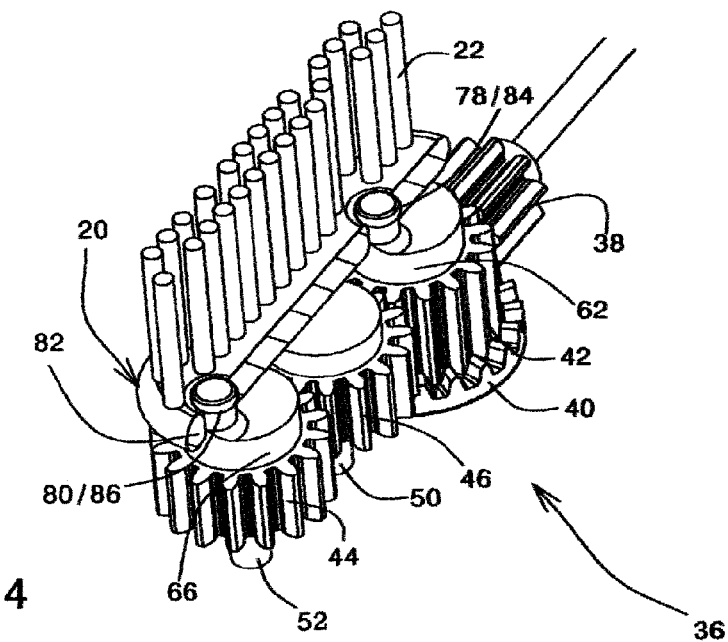
FIG. 4 is an isometric projection of the movement of the embodiment of FIG. 3, coupled to a brush head (shown in cutaway section)
Figure 5:
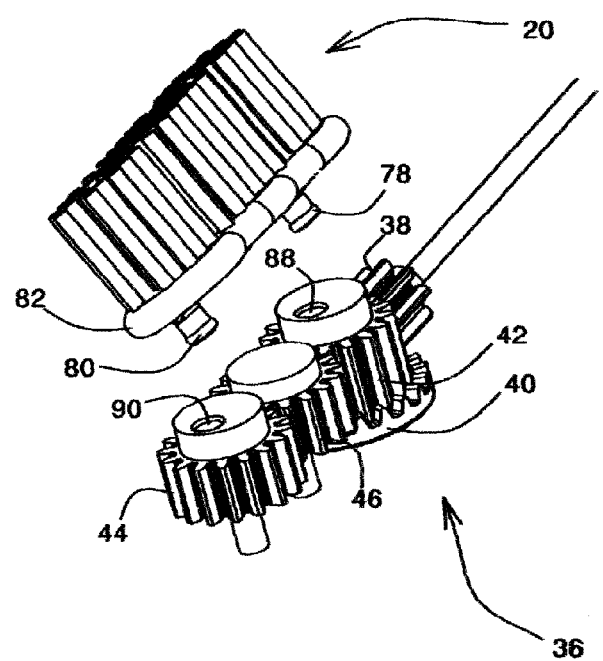
FIG. 5 is an isometric projection showing the movement of an alternative embodiment, and a brush, where the eccentric pins are fixed to the brush and engage socket holes in the master and slave gears of the movement.

FIG. 4 shows the assembled movement 36 of the embodiment of FIG. 3, coupled to the brush head 20 shown in cutaway section. As shown in FIG. 5, however, in an alternative embodiment, the eccentric pins 78, 80 may be fixed to the brush back plate 82 of brush 20, and engage socket holes 88, 90 in the master and slave gears 42, 46 of the movement 36.

To hold the brush 20 in place, the eccentric pins 78, 80 are preferably split pins that lockingly engage the socket holes 84, 86 (or 88, 90). For ease of fabrication the eccentric pins 78, 80 will typically be fabricated integrally with either the master and slave gears 42, 46 or with the brush back plate 82 however.

The various bristle clusters 22 of the brush 20 may be identical or different, and any of the bristle arrays of the prior art may be used, particularly the recent manual toothbrush bristle arrays, having clusters of bristles of two or more different types.

The intermediate gear 46 shown may be replaced by other transmission systems to couple the master and slave gears, such as a drive belt, or an odd numbered chain of gears for example. In this manner, the diameter of the master and slave gears may be varied somewhat as may their separation. Since their angular velocity may be set, the brushing peed, and size and shape of the orbital brushing path may be optimized for different brush sizes, age and mouth size of user, and the like.

The brush 20 is preferably detachable from the master and slave gears 42, 46 by insertion of a knife blade between brush back plate 82 and facing plate 74. In this manner, the user may replace the relatively small and simple brush 20 section only, once worn, and thereby obtain what is effectively a new brush. Optionally the mechanical toothbrush of the invention may be provided with a set of interchangeable brushes 20, perhaps one brush optimized for brushing removable oral prosthetics such as dentures, orthodontic brace plates and the like, and a second brush for brushing the teeth.

To enable the mechanical toothbrush base section, including handle and motor, to be used by different users, such as family members, preferably the whole distal end of the toothbrush may be separated from the handle unit and replaced with another distal end section.

Since only the brush 20 itself moves against the teeth, the mechanical toothbrush 10 of the present invention is remarkably efficient, and little energy is wasted by vibrating the whole distal end section 14 back and forth, against the inside cheek of the user. Furthermore, toothbrushes in accordance with the present invention tend to be remarkably quiet in operation.

Although the toothbrush distal end of the present invention is described hereinabove as being coupled to a battery operated driving means within the handle 12, it will be appreciated that electrical toothbrushes including the present invention may be mains powered. Indeed, the driving means could conceivably be hydraulic or pneumatic, such as sometimes provided in dental surgeries. Thus persons skilled in the art will appreciate that the present invention is not limited to what has been particularly shown and described hereinabove. Rather the scope of the present invention is defined by the appended claims and includes both combinations and subcombinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other component.

What is claimed is:

1. A toothbrush distal end for attachment to a handle of a mechanical toothbrush including a driving means; the distal end comprising:
a head;
a neck having a proximal end and a distal end;
a drive shaft having a driving bevelled gear fixed to distal end thereof;
a brush consisting of a bristle array on a brush back plate, and
a movement;
the head being fixedly attached to the distal end of the neck;
the neck being detachably couplable to the handle;
the neck being hollow and serving as a sleeve for the drive shaft;
the drive shaft being rotatingly drivable about its axis within the neck, by the driving means;
wherein the movement is situated within a cavity in the head and is connected to the brush back plate, for moving the brush back plate along an elliptical orbital path with respect to the head when driven by the driving means via the rotating drive shaft;
the movement comprising:
a driven bevelled gear;
a master gear;
a transmission system;
a slave gear;
a first eccentric pin being eccentrically attachable to the master gear;
a second eccentric pin being eccentrically attachable to the slave gear;
the first and second eccentric pins for attachment of the brush back plate to the movement;
the driven bevelled gear being drivenly coupled to the driving bevelled gear of the drive shaft,
the driven bevelled gear being coupled to the master gear, such that the driven bevelled gear drives the master gear and the master gear drives the slave gear via the transmission, for rotating the master gear and the slave gear together in the same direction;
the eccentric pins driving the brush in the elliptical orbital path.

2. The toothbrush distal end of claim 1, said transmission being an intermediate gear, said master gear, intermediate gear and slave gear rotating around axles that engage inside back wall of the cavity in the toothbrush head;
the driven bevelled gear being coaxially joined to the master gear; each eccentric pin passing through an aperture in face of toothbrush head, and connecting to back of brush back plate.

3. The toothbrush distal end of claim 2 wherein said axles are fixedly connected to back of toothbrush head and said master, slave and intermediate gears freely rotate round their axles.

4. The toothbrush distal end of claim 2 wherein said axles are fixedly connected to master, slave and intermediate gears and loosely engage sockets on back of toothbrush head, freely rotating with respect to said sockets.

5. The toothbrush distal end of claim 2 wherein said eccentric pins are fixedly connected to said master and slave gears and loosely engage holes on brush back plate.

6. The toothbrush distal end of claim 5 wherein said eccentric pins are split pins that clip fit into the holes.

7. The toothbrush distal end of claim 2 wherein said eccentric pins are fixedly connected to said brush back plate and loosely engage socket holes in said master, slave and intermediate gears freely rotating with respect to said socket holes.

8. The toothbrush distal end of claim 7 wherein said eccentric pins are split pins that clip fit said socket holes.

9. The toothbrush distal end of claim 1, said driving means comprising a motor and power source.

10. The toothbrush distal end of claim 9, the motor and power source being situated within the handle.

11. The toothbrush distal end of claim 9, the power source being selected from the list of: a power supply coupled to an electric main, a single use battery and a rechargeable battery.

12. The toothbrush distal end of claim 1, said driving means being selected from the list of hydraulic driving means, pneumatic driving means and electrical driving means, the distal end connecting to a handle of a professional dental tool.

13. The toothbrush distal end of claim 1 being permanently fixed to a handle.

14. The toothbrush distal end of claim 1 being removably attachable to a handle.

* * * * *